(12) United States Patent
McKenna

(10) Patent No.: US 9,386,931 B2
(45) Date of Patent: Jul. 12, 2016

(54) SYSTEM AND METHOD FOR RECEIVING AN INDICATION OF PROPER BODY LOCATIONS OF SENSORS ON A PATIENT

(75) Inventor: Edward M. McKenna, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 1647 days.

(21) Appl. No.: 12/751,785

(22) Filed: Mar. 31, 2010

(65) Prior Publication Data

US 2011/0245622 A1 Oct. 6, 2011

(51) Int. Cl.
*G06F 15/18* (2006.01)
*A61B 5/024* (2006.01)
*G06F 19/00* (2011.01)
*A61B 5/021* (2006.01)
*A61B 5/0402* (2006.01)
*A61B 5/00* (2006.01)

(52) U.S. Cl.
CPC .......... *A61B 5/02416* (2013.01); *A61B 5/7267* (2013.01); *G06F 19/3406* (2013.01); *A61B 5/021* (2013.01); *A61B 5/0402* (2013.01); *A61B 5/684* (2013.01); *A61B 5/726* (2013.01); *A61B 2560/029* (2013.01)

(58) Field of Classification Search
USPC ............................................. 706/12, 45, 62
See application file for complete search history.

(56) References Cited

U.S. PATENT DOCUMENTS

| | | | |
|---|---|---|---|
| 6,035,223 A | 3/2000 | Baker, Jr. | |
| 6,308,089 B1 | 10/2001 | von der Ruhr et al. | |
| 6,388,240 B2 | 5/2002 | Schulz et al. | |
| 6,515,273 B2 | 2/2003 | Al-Ali | |
| 6,560,470 B1 | 5/2003 | Pologe | |
| 6,861,639 B2 | 3/2005 | Al-Ali | |
| 6,979,812 B2 | 12/2005 | Al-Ali | |
| 7,048,687 B1 | 5/2006 | Reuss et al. | |
| 7,186,966 B2 | 3/2007 | Al-Ali | |
| 7,596,535 B2 * | 9/2009 | de Voir et al. | 706/20 |
| 2001/0045509 A1 | 11/2001 | Al-Ali | |
| 2003/0135099 A1 | 7/2003 | Al-Ali | |
| 2005/0289092 A1 * | 12/2005 | Sumner et al. | 706/46 |
| 2006/0206020 A1 | 9/2006 | Liao et al. | |
| 2007/0156034 A1 | 7/2007 | Al-Ali | |
| 2008/0058622 A1 * | 3/2008 | Baker | 600/344 |

(Continued)

FOREIGN PATENT DOCUMENTS

| | | |
|---|---|---|
| JP | 2007020836 | 2/2007 |
| JP | 2007330708 | 12/2007 |

OTHER PUBLICATIONS

Otto et al., System Architechure of a wireless body area sensor network for ubiquitous health monitoring, 2006, Rinton PRess pp. 1-20.*

(Continued)

*Primary Examiner* — David Vincent
(74) *Attorney, Agent, or Firm* — Fletcher Yoder PC

(57) ABSTRACT

Systems, methods, and devices for determining whether a medical sensor has been properly applied to a patient are provided. In one embodiment, a patient monitor having such capabilities may include a medical sensor interface and data processing circuitry. The medical sensor interface may receive physiological data from a medical sensor applied to a patient. The data processing circuitry may be capable of being trained, using a learning-based algorithm, to determine whether the received physiological data indicates that the medical sensor has been properly applied to the patient.

9 Claims, 11 Drawing Sheets

(56) References Cited

U.S. PATENT DOCUMENTS

| | | |
|---|---|---|
| 2008/0081967 A1 | 4/2008 | Andersohn et al. |
| 2008/0081971 A1 | 4/2008 | Ollerdessen |
| 2008/0088467 A1 | 4/2008 | Al-Ali |
| 2008/0221414 A1 | 9/2008 | Baker |
| 2009/0163787 A1* | 6/2009 | Mannheimer et al. ........ 600/324 |
| 2009/0254281 A1* | 10/2009 | Hruska et al. .................... 702/7 |
| 2010/0152594 A1* | 6/2010 | Bhat et al. ..................... 600/501 |
| 2010/0198521 A1* | 8/2010 | Haick ............................ 702/19 |
| 2012/0143805 A1* | 6/2012 | Gold et al. ..................... 706/20 |

OTHER PUBLICATIONS

Anliker et al., Design Methodology for Context-Aware Wearable Sensor Systems, 2005, Springer-Verlag, pp. 1-17.*
Mallat, A Wavelet Tour of Signal Processing, 1999, Elsevier, pp. 1, 17, 326-344.*

* cited by examiner

SYSTEM AND METHOD FOR RECEIVING AN INDICATION OF PROPER BODY LOCATIONS OF SENSORS ON A PATIENT

BACKGROUND

The present disclosure relates generally to techniques for using medical sensors and, more particularly, to techniques for determining proper placement of medical sensors on a patient body location.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Medical sensors are used to obtain a variety of patient physiological parameters. For example, a properly applied photoplethysmographic sensor may provide such information as patient pulse rate, blood oxygen saturation, and/or total hemoglobin. When a medical sensor is improperly applied, however, data received from the medical sensor may not accurately reflect the state of the patient. Moreover, certain physiological measurements, such as pulse transit time or an electrocardiogram (ECG), may depend on knowledge of the body location where medical sensors are applied. If a sensor has been applied to an incorrect body location, calculated physiological measurements based on data from the sensor may also be incorrect.

SUMMARY

Certain aspects commensurate in scope with the originally claimed embodiments are set forth below. It should be understood that these aspects are presented merely to provide the reader with a brief summary of certain forms the embodiments might take and that these aspects are not intended to limit the scope of the presently disclosed subject matter. Indeed, the embodiments may encompass a variety of aspects that may not be set forth below.

Present embodiments relate to systems, methods, and devices for determining whether a medical sensor has been properly applied to a correct body location of a patient and/or whether the patient has a known disease or condition. In one embodiment, a patient monitor having such capabilities may include a medical sensor interface and data processing circuitry. The medical sensor interface may receive physiological data from a medical sensor applied to a patient. The data processing circuitry may be capable of being trained, using a learning-based algorithm, to determine whether the received physiological data indicates that the medical sensor has been properly applied to the patient.

BRIEF DESCRIPTION OF THE DRAWINGS

Advantages of the presently disclosed subject matter may become apparent upon reading the following detailed description and upon reference to the drawings in which.

DETAILED DESCRIPTION

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments may apply to a variety of medical sensors, including photoplethysmographic sensors, temperature sensors, respiration bands, blood pressure sensors, electrocardiogram (ECG) sensors, pulse transit time sensors, and so forth. Such sensors may obtain a variety of physiological measurements based on information detected from patient tissue. By applying a learning-based algorithm using sensor data obtained over a population of patients, a medical sensor system may be trained to identify certain characteristics associated with sensors for placement at various patient body locations. Such a trained medical sensor system may be able to determine, for example, when a medical sensor has been placed in the correct location on a patient, has been properly applied, and/or has recovered data from a patient indicating the patient has a condition or disease. In some embodiments, the medical sensor system may identify classes of similar plethysmographic waveforms, for example, by comparing measured characteristics of each waveform or identifying image patterns in scalograms obtained by performing a wavelet transform on the plethysmographic waveforms. These classes may be stored and compared against physiological data from a medical sensor to determine whether the medical sensor is properly applied.

Figure 1:
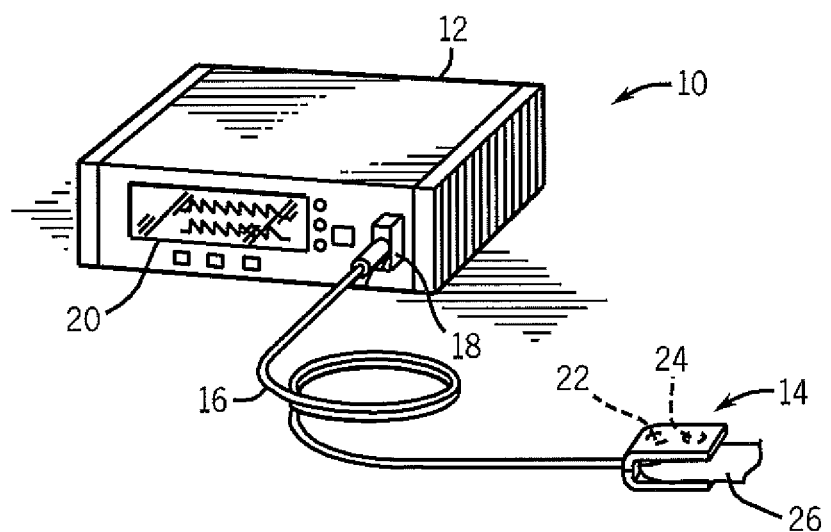
FIG. 1 is a perspective view of a medical sensor system, in accordance with an embodiment.

With the foregoing in mind, FIG. 1 is a perspective view of a medical sensor system 10 that may be trained, using a learning-based algorithm, to determine when a medical sensor has been placed in the correct location on a patient, has been properly applied, and/or has recovered data from a patient indicating the patient has a condition or disease. Although the embodiment of the medical sensor system 10 illustrated in FIG. 1 involves a photoplethysmographic monitor 12 and sensor 14, additionally or alternatively, the medical sensor system 10 may be configured for use with any suitable medical sensor. Such medical sensors may include, for example, temperature sensors, respiration bands, blood pressure sensors, electrocardiogram (ECG) sensors, pulse transit time sensors, and so forth.

The system 10 may include a patient monitor 12 that communicates with a medical sensor 14 using a sensor cable 16 attached via a monitor-cable connection 18. The patient monitor 12 may include a display 20, memory, a processor, and various monitoring and control features. Based on sensor data received from the medical sensor 14, the patient monitor 12 may display patient parameters and perform various additional algorithms. Among other things, the patient monitor 12 may "learn" what data to expect from a given type of medical sensor 14 using a learning-based algorithm. Learning based algorithms can be supervised or unsupervised or a combination of both. Supervised techniques may include Artificial Neural Networks (ANN), Support Vector Machines (SVM) and Naïve Bayes Classifiers. Unsupervised techniques may include self organizing maps, adaptive resonance and clustering techniques (K-Means). Certain embodiments of such learning-based algorithms are described below with reference to FIGS. 7 and 15. Training the medical sensor system 10 using such a learning-based algorithm may enable the medical sensor system 10 to determine whether the medical sensor 14 has been placed in the proper location, has been properly applied, and/or has received data indicative of a known condition or disease. For example, the patient monitor 12 may ascertain whether a photoplethysmographic waveform obtained from the medical sensor 14 matches what the patient monitor 12 has "learned" the waveform should look like when properly applied to the correct location on a patient's body. If the patient monitor 12 determines that the obtained photoplethysmographic waveform indicates proper placement and application, the patient monitor 12 may provide such indication on the display 20 or via a beep or other sound.

In the presently illustrated embodiment of the system 10, the medical sensor 14 is a photoplethysmographic finger sensor. Additionally or alternatively, however, the sensor 14 may be a photoplethysmographic sensor for placement on another patient body location, a temperature sensor, a respiration band, a blood pressure sensor, an ECG sensor, or a pulse transit time sensor, and so forth. The medical sensor 14 may attach to patient tissue (e.g., a patient's finger, ear, forehead, or toe). In the illustrated embodiment, the medical sensor 14 is configured to attach to a finger.

The medical sensor 14, illustrated in the present embodiment as a photoplethysmographic sensor, may include an emitter 22 and a detector 24. When attached to pulsatile tissue, the emitter 22 may emit light at certain wavelengths into the tissue and the detector 24 may receive the light after it has passed through or is reflected by the tissue. For example, the medical sensor 14 may emit light from two or more light emitting diodes (LEDs) or other suitable light sources into the pulsatile tissue. The reflected or transmitted light may be detected by the detector 24, which may be, for example, a photodiode or photo-detector. The amount of light that passes through the tissue, as well as other characteristics of the light, may vary in accordance with the changing amount of certain blood constituents in the tissue and the related light absorption and/or scattering. In some embodiments, the medical sensor system 10 may utilize a medical sensor 14 that employs photon density waves (PDW) signals to ascertain physiological parameters and to obtain photoplethysmographic waveforms.

Figure 2:
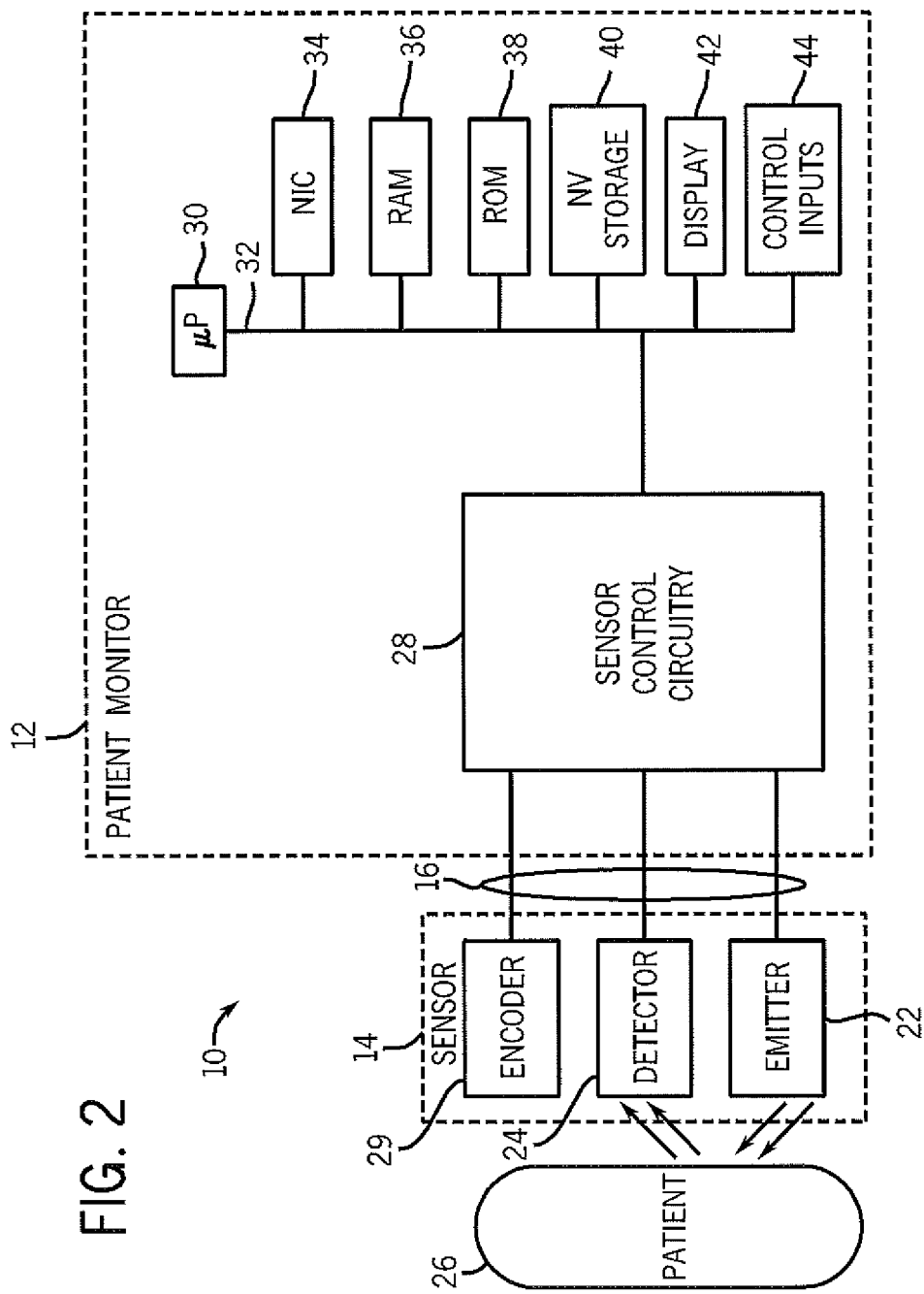
FIG. 2 is a block diagram of the medical system of FIG. 1, in accordance with an embodiment.

FIG. 2 is a block diagram of an embodiment of the medical sensor system 10 of FIG. 1. By way of example, embodiments of the system 10 may be implemented with any suitable medical sensor and patient monitor, such as those available from Nellcor Puritan Bennett LLC. The system 10 may include the patient monitor 12 and the medical sensor 14, and may obtain, for example, a photoplethysmographic signal from the pulsatile tissue of a patient 26.

Sensor interface circuitry 28 in the patient monitor 12 may interface with the medical sensor 14. By way of example, the sensor interface circuitry 28 may generate an emitter 22 control signal using light drive circuitry, causing the emitter 22 to emit light of certain wavelengths into the patient 26. The detector 24 may detect light that is transmitted or reflected through the patient 26 and may return an output signal to the sensor interface circuitry 28. Amplification, low pass filter, and analog-to-digital conversion circuitry in the sensor interface circuitry 28 may amplify and digitize the received output signal from the detector 24.

In some embodiments, the medical sensor 14 may also include an encoder 29 that provides signals indicative of the wavelength of one or more light sources of the emitter 22, which may allow for selection of appropriate calibration coefficients for calculating a physiological parameter such as blood oxygen saturation. The encoder 29 may, for instance, be a coded resistor, EEPROM or other coding devices (such as a capacitor, inductor, PROM, RFID, parallel resonant circuits, or a colorimetric indicator) that may provide a signal indicative of the characteristics of the photoplethysmographic sensor 14 to a detector/decoder in the sensor interface circuitry 28. Additionally or alternatively, the encoder 29 may provide a code that indicates, for example, the type of sensor (e.g., photoplethysmographic) and/or the body location where the sensor 14 is intended to be applied (e.g., finger).

As shown in FIG. 2, the patient monitor 12 may include a general- or special-purpose microprocessor 30 on a bus 32, which may govern various operations of the patient monitor 12. Such operations may include the determination of various physiological parameters based on data from the medical sensor 14, as well whether the medical sensor 14 has been properly located and applied on the patient 26. A network interface card (NIC) 34 may enable the patient monitor 12 to communicate with external devices on a network. Random access memory (RAM) 36 may provide temporary storage of variables and other data employed while carry out certain techniques described herein, while read only memory (ROM) 38 may store certain algorithms, such as the disclosed learning-based algorithms and those used by for determining proper medical sensor 14 location and application. Though nonvolatile storage 40 generally may store long-term data, the nonvolatile storage 40 also may store the algorithms described herein.

The patient monitor 12 may include other components, such as a display interface 42 and control inputs 44. The display interface 42 may enable the patient monitor 12 to indicate on the display 20 whether the medical sensor 14 has been properly applied and located on the patient 26. Control inputs 44 may enable a physician or other medical practitioner to vary the operation of the patient monitor 12.

Data obtained from a medical sensor 14 may vary depending on the location and application of the sensor 14 on the patient 26. In one example, described below with reference to FIGS. 3-6, data obtained from a finger sensor may differ from a forehead sensor in predictable ways. The patient monitor 12 may be trained using a learning-based algorithm, such as those described below with reference to FIGS. 7 and 8, to identify such differences. Thereafter, the patient monitor 12 may determine when a given medical sensor 14 has been properly located and applied.

Figure 3:
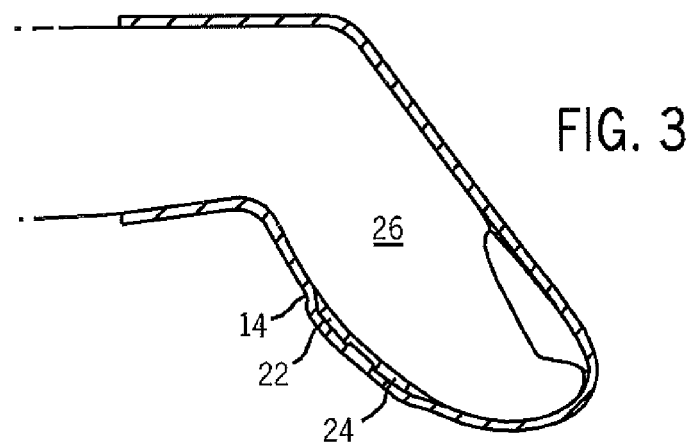
FIG. 3 is a schematic cross-sectional view of a finger pulse oximetry sensor for use with the medical sensor system of FIG. 1, in accordance with an embodiment.

FIG. 3 illustrates a schematic cross-sectional view of an embodiment in which the medical sensor 14 is a photoplethysmographic finger sensor. The emitter 22 of the sensor 14 may emit one or more wavelengths of light into the tissue of the patient 26. The light may be scattered and reflected back to the detector 24. Signals representative of the detected light may be transmitted to the patient monitor 12, which may be used to generate an optical digit plethysmograph 46, one embodiment of which is illustrated in FIG. 4.

Figure 4:
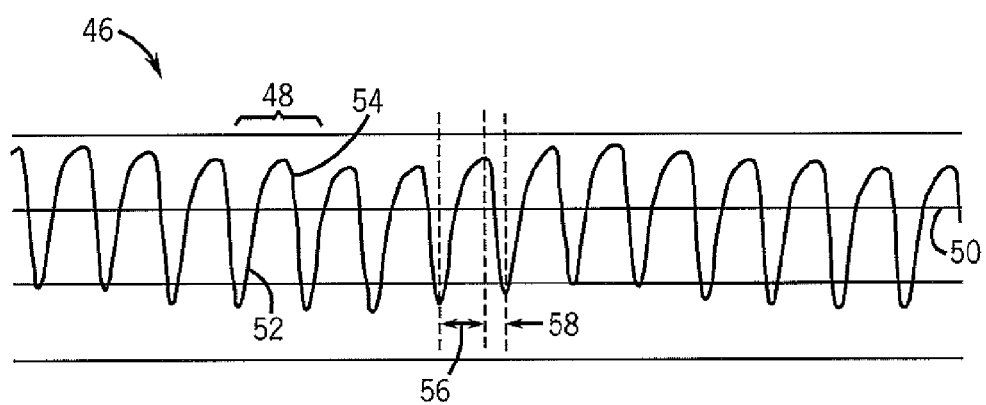
FIG. 4 is a representative plethysmographic signal obtained using the finger pulse oximetry sensor of FIG. 3, in accordance with an embodiment.

In the optical digit plethysmograph 46 of FIG. 4, high-frequency pulses 48 generally vary around an average value, represented as an average value line 50. The average value line 50 may represent an average, weighted average, mean, median, or mode of pulse 48 measurements. Each pulse 48 may represent the pulse of the patient 26, and may include a diastolic component 52 and a systolic component 54. In general, the systolic component 54 of the optical digit plethysmograph 46 may correspond generally to the minima of the waveform, since increasing blood volume may absorb more light and may reduce the amount of reflected light that reaches the detector 24. The diastolic component 52 may represent the time during which the heart is relaxed and dilating, causing blood to enter the heart, while the systolic component 54 represents the time during which the heart is contracting, causing blood to be expelled from the heart. In the presence of only arterial pulsation, as in the optical digit plethysmograph 46, the diastolic component 52 may have a longer time component 56 compared to a time component 58 of the systolic component 54. That is, the time 56 it takes for the signal to reach a peak may be greater than the time 58 it takes for the signal to reach a valley, corresponding to maximum blood volume. A histogram of the derivative of the pulse 48 may have a negative skew because the shorter systolic component 54 creates a negative derivative of greater magnitude than a positive derivative occurring during the diastolic component 52.

Figure 5:
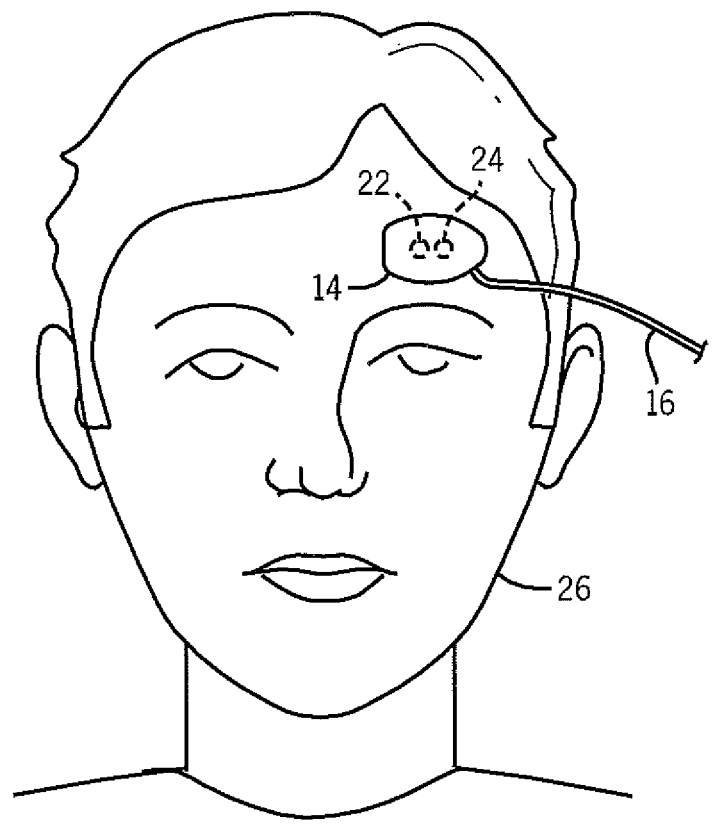
FIG. 5 is a perspective view of a forehead pulse oximetry sensor for use with the medical sensor system of FIG. 1, in accordance with an embodiment.

In comparison, FIG. 5 represents an embodiment in which the medical sensor 14 is a photoplethysmographic forehead sensor. Like the embodiment of the medical sensor 14 of FIG. 3, the emitter 22 of the sensor 14 of FIG. 5 may emit one or more wavelengths of light into the tissue of the patient 26. The light may be scattered and reflected back to the detector 24. Signals representative of the detected light may be transmitted to the patient monitor 12, which may be used to generate an optical forehead plethysmograph 46, one embodiment of which is illustrated in FIG. 6.

Figure 6:
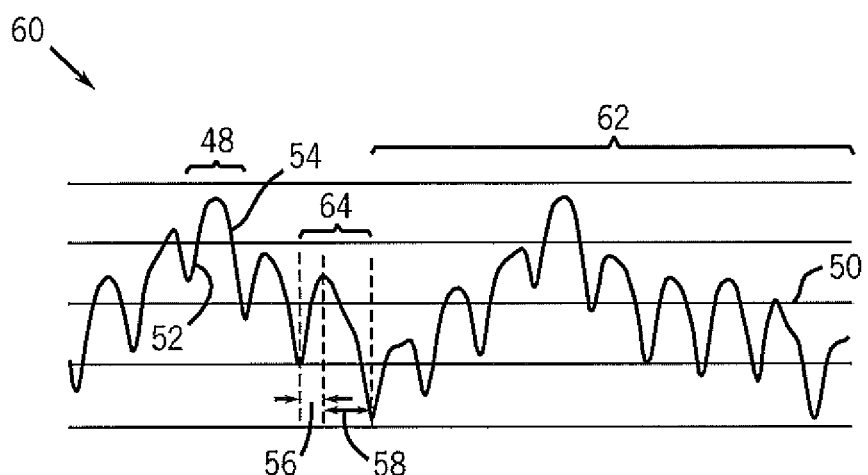
FIG. 6 is a representative plethysmographic signal obtained using the forehead pulse oximetry sensor of FIG. 3, in accordance with an embodiment.

In the optical forehead plethysmograph 60 of FIG. 6, the pulse of the patient 26 is represented by a high-frequency function with short pulses 48. In addition to this high-frequency function, a low-frequency function is also apparent in the forehead plethysmograph 60, illustrated as a low-frequency wave 62 that varies around the average value line 50. It is believed that this low-frequency wave 62 may correspond to the respiratory rate of the patient 26. As the patient 26 inhales, the diaphragm may contract and reduce pressure on the thoracic cavity. This reduced pressure may increase the return flow of blood into the veins in the thoracic cavity from peripheral areas of the body. This venous flow particularly may affect local blood volume in other areas of the body, such as the head, which are in open communication with the thoracic veins.

In addition, due to the presence of both arterial and venous pulsation, the diastolic component 52 and the systolic component 54 of the pulse 48 do not behave in the same manner as in the presence of arterial pulsation alone. That is, in some pulses 48, the diastolic time component 56 may be shorter than the systolic time component 58, as illustrated by a pulse 64. A histogram of the derivative of the pulse 64 may have a positive skew because the diastolic component 52 creates a positive derivative that is larger in magnitude than a negative derivative of the longer systolic component 54.

Furthermore, in the presence of venous pulsation, the forehead plethysmograph 60 may exhibit a preponderance of high-frequency energy due to harmonics in the venous pressure wave. That is, the pulses 48 may appear to have bumps (not shown) as a result of a high-frequency function at a harmonic of the pulse rate. Generally, this phenomenon may be most pronounced at the second and third harmonics of the pulse rate.

Distinctions based on the location of the medical sensor 14 on a patient 26, such as the differences between the photoplethysmographic waveforms 46 and 60, may enable the patient monitor 12 to determine when the medical sensor 14 is properly located and applied on the patient 26. It should be appreciated, however, that the examples illustrated in FIGS. 3-6 are intended to be representative and not exclusive. Indeed, whether the medical sensor 14 is a photoplethysmographic or non-photoplethysmographic sensor, obtained sensor data may vary depending on the location of the medical sensor 14 on the patient 26. In other examples, body temperature, electrocardiogram (ECG) signals, blood pressure, pulse transit time, and so forth, may also vary predictably depending on a body location of a patient 26 where the sensor 14 has been applied.

Figure 7:
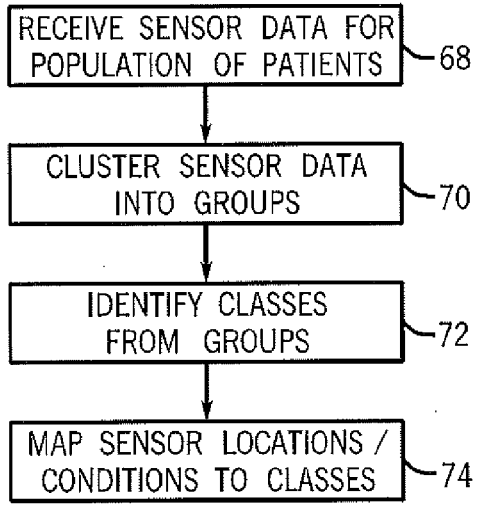
FIG. 7 is a flowchart representing an embodiment of a method for training the medical sensor system of FIG. 1 using a learning-based algorithm.

When sensor data is collected over a population of patients 26 for which the location and proper application of the sensor 14 is known, the medical sensor system 10 may use a learning-based algorithm with such collected data to "learn" what sensor data from each location should look like. FIG. 7 is a flowchart 66 describing one embodiment of such a learning-based algorithm. The steps of the flowchart 66 may be implemented in code stored on a tangible machine-readable medium, such as the ROM 38 or non-volatile storage 40.

In a first step 68, the patient monitor 12 may receive sensor data collected from a population of patients 26. Demographic data associated with the collected sensor data may indicate the body location of the sensor 14 from which the data was collected, the age of the patient 26, any conditions or diseases the patient 26 experienced while sensor data was obtained, and so forth. In some embodiments, the collected sensor data may include sensor data obtained simultaneously from two or more medical sensors 14, the combination of which may indicate a relationship that, using the instant technique, may become apparent from the training of the medical sensor system 10. The sensor data received by the patient monitor in step 68 may derive from a database of previously-obtained sensor data, or may be obtained directly from patients 26 monitored by the medical sensor system 10.

In step 70, the patient monitor 12 may cluster the sensor data received in step 68 into different groups. These groups may be based on similar average sensor values (e.g., an average temperature, signal polarity, or an average or DC value of a plethysmograph), time- or frequency-dependent changes in sensor data (e.g., high-frequency or low-frequency components of a plethysmograph), or any other detected similarities (e.g., generally occurring at certain times of day). Any suitable number of groups of like sensor data may be ascertained from the sensor data received in step 68.

In step 72, the patient monitor 12 may create sensor data classes based on the groups determined in step 70. The sensor data classes created in step 72 may represent common characteristics of the sensor data groups (e.g., an average physiological value or waveform frequency). At a later time, when the patient monitor 12 is collecting sensor data from a medical sensor 14 applied to a patient 26, the patient monitor 12 may compare the subsequently-obtained sensor data to the characteristics represented by the various classes, as generally described below with reference to FIG. 8.

Each class may be based on one or more groups of sensor data, or each class may be based on only a subset of a group. The patient monitor 12 may select the classes to sufficiently encompass commonalties between sensor data from a given body location in which the sensor 14 was placed and/or between sensor data from patients 26 having certain diseases, conditions, ages, and so forth. By way of example, some of the classes may correspond to sensor data associated with the proper application of a plethysmographic finger sensor or forehead sensor in a generally healthy patient 26, and some of the classes may correspond to sensor data associated with diseases or conditions, such as anesthesia effects. In some embodiments, certain classes may be associated with sensor data from a misapplied medical sensor 14.

The range and types of classes that the patient monitor 12 may create may be predefined or may be determined based on demographic data available for the population of patients 26 from which the sensor data was obtained. As such, in some embodiments, the patient monitor 12 may select classes based on unexpected patterns that may emerge when the sensor data is clustered into groups in step 70. For example, if certain groups identified in step 70 indicate common sensor data properties among patients of a certain age or geographic location, the patient monitor 12 may select classes that correspond to such demographic criteria.

After the classes have been ascertained in step 72, the patient monitor 12 may map or associate the identified classes to the body location where sensor data was obtained (e.g., finger, toe, or forehead), any diseases or conditions indicated by the class of sensor data (e.g., under anesthesia), and/or certain demographic data (e.g., age 60 or older) in step 74. When step 74 has ended, the patient monitor 12 may store the mapped classes in the RAM 36, non-volatile storage 40, or on an external device. These mapped classes may be recalled at a later time to determine whether a medical sensor 14 has been properly located on and applied to a patient 26. A patient monitor 12 that has completed the steps of the flowchart 66 of FIG. 7 may be understood to have been "trained" to identify the characteristics of the mapped classes in other received sensor data.

Figure 8:
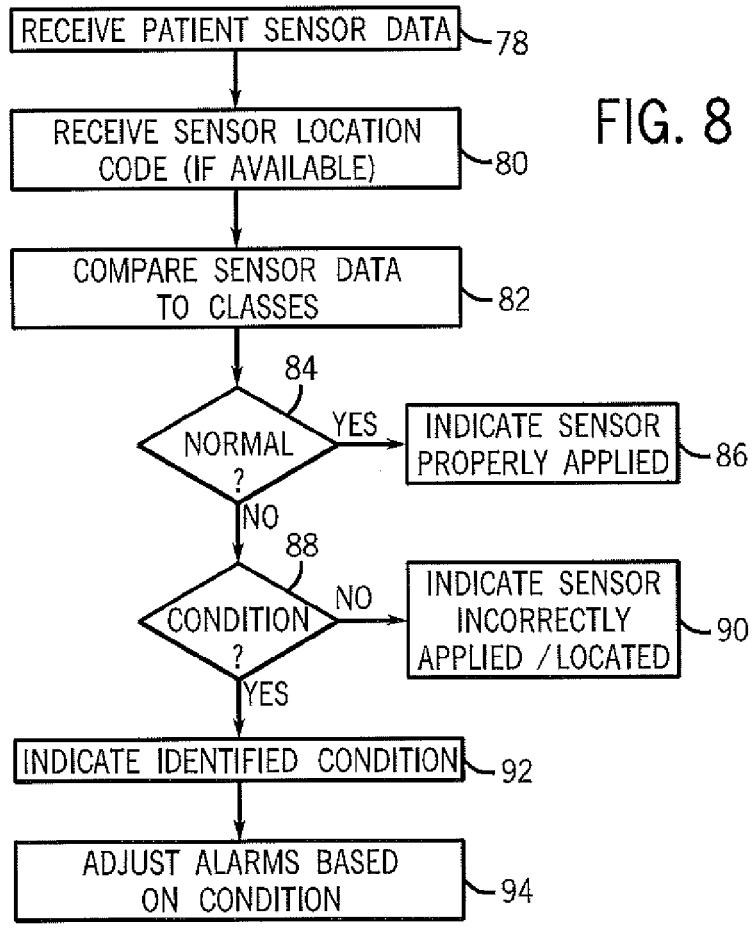
FIG. 8 is a flowchart representing an embodiment of a method for ascertaining sensor application status using the medical sensor system of FIG. 1 after training.

FIG. 8 is a flowchart 76 representing one embodiment of a method for using a patient monitor 12, trained using the technique of FIG. 7, to determine whether a medical sensor 14 has been properly located on and applied to a patient 26 and/or whether the patient 26 has a known condition or disease. The embodiment of the method represented by FIG. 8 is intended to representative and not exclusive, as the trained patient monitor 12 may employ any suitable technique to ascertain proper sensor application based on a comparison of received sensor data to previously identified classes of sensor data.

In a first step 78, the patient monitor 12 may receive physiological sensor data from a medical sensor 14 applied to a body location of a patient 26. Some medical sensors 14 may transmit a code or other indication to the patient monitor 12 that describes the intended location of the medical sensor. If such information is available, the patient monitor 12 may receive such a code in step 80, which may occur before or after step 78.

In step 82, the patient monitor 12 may compare the sensor data received in step 78 to the identified classes stored in the RAM 36, the non-volatile storage 40, and/or an external device. From step 80, the patient monitor 12 may have an indication of the intended body location of the medical sensor 14. Thus, as indicated by decision block 84, if the received sensor data shares a sufficient threshold of characteristics with a class representing sensor data from medical sensors properly applied to the same body location on healthy individuals, the patient monitor 12 may output an indication that the medical sensor 14 has been properly applied in step 86. The indication may include a message on the display 16, a beep, and/or a flashing light, and so forth.

Turning again to decision block 84, if the received sensor data does not share a sufficient threshold of characteristics with a class representing sensor data from medical sensors properly applied to the same body location on healthy individuals, the process may flow to decision block 88. In decision block 88, the patient monitor 12 may consider whether the sensor data shares a sufficient threshold of characteristics with a class indicating a disease or condition. If not, the patient monitor 12 may conclude that the medical sensor 14 has not been properly applied and, in step 90, may output an indication that the medical sensor 14 has not been properly applied and/or located. If, in decision block 88, the patient monitor 12 does identify the sensor data as indicative of a disease or condition, the patient monitor 12 may provide an indication of the identified condition or disease in step 92. The patient monitor 12 may also modify its operation to account for the particular disease or condition in step 94. By way of example, in step 94, the patient monitor 12 may adjust alarm thresholds, increase or decrease sensor data rates, and so forth.

To provide one example, if the medical sensor 14 is a finger sensor, such as the finger sensor described in FIG. 3, the patient monitor 12 may analyze certain characteristics of a photoplethysmographic signal received from the sensor 14, such as values associated with high-frequency and low-frequency components of the signal. These characteristics may be distinct from previously identified classes that include, for example, sensor data from properly applied forehead sensors, but may be sufficiently similar to sensor data from other finger sensors. Thus, the patient monitor 12 may identify the medical sensor 14 as properly located and applied, and may provide an indication as such.

Figure 13:
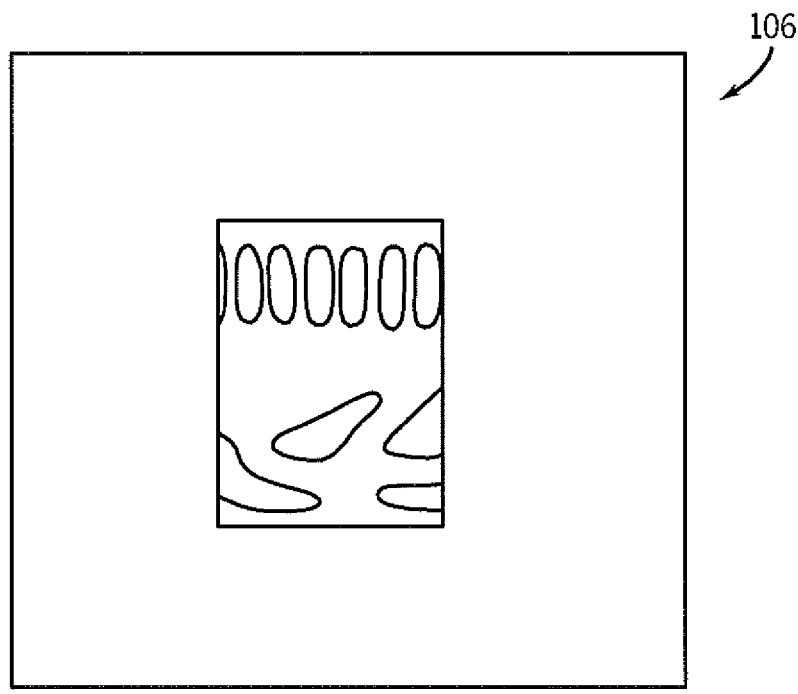
Figure 14:
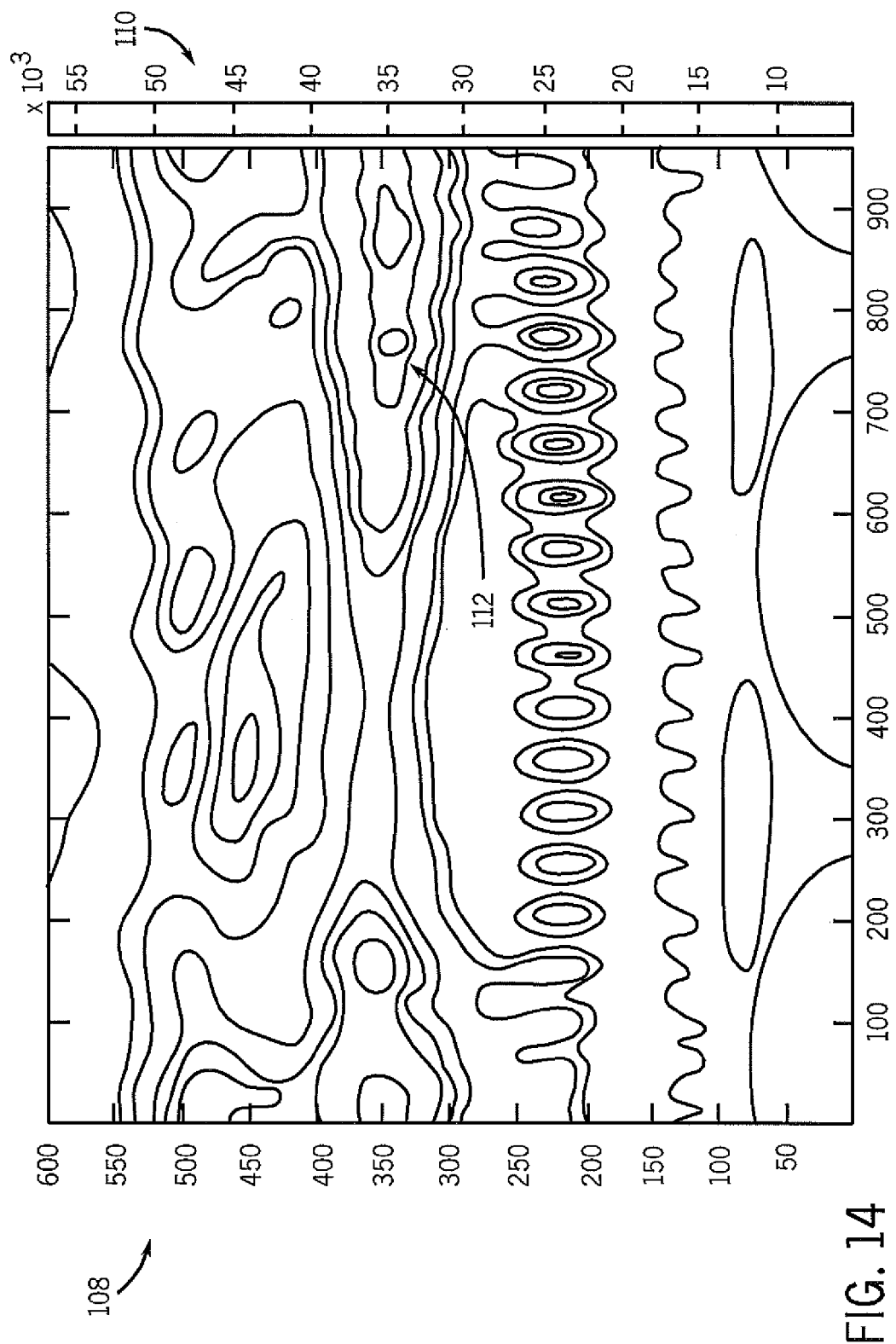
Figure 15:
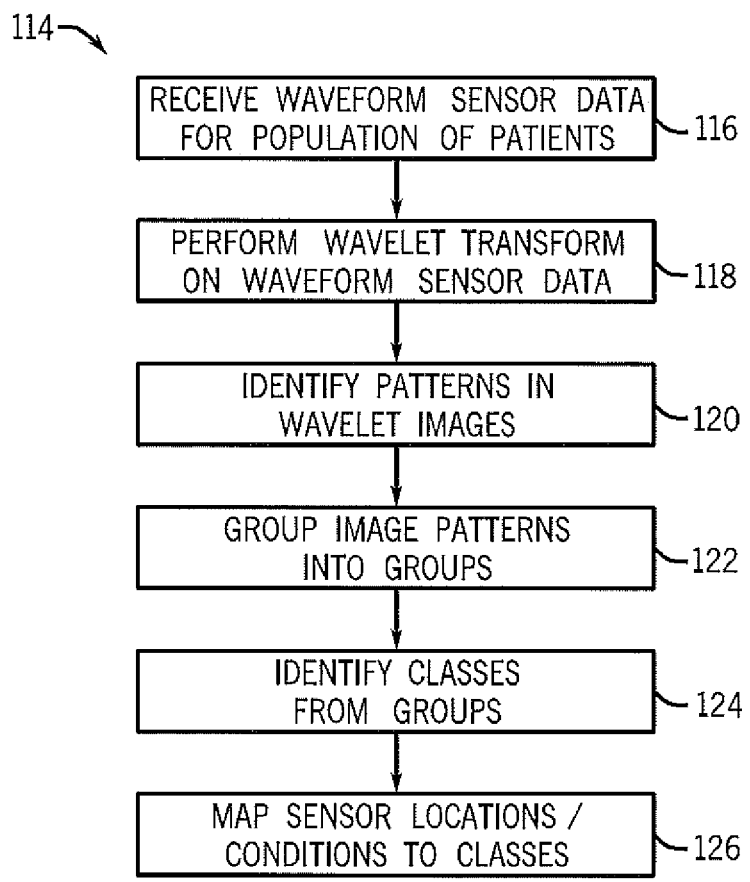
FIG. 15 is a flowchart representing an embodiment of a method for training the medical sensor system of FIG. 1 for wavelet image pattern detection using a learning-based algorithm.
Figure 16:
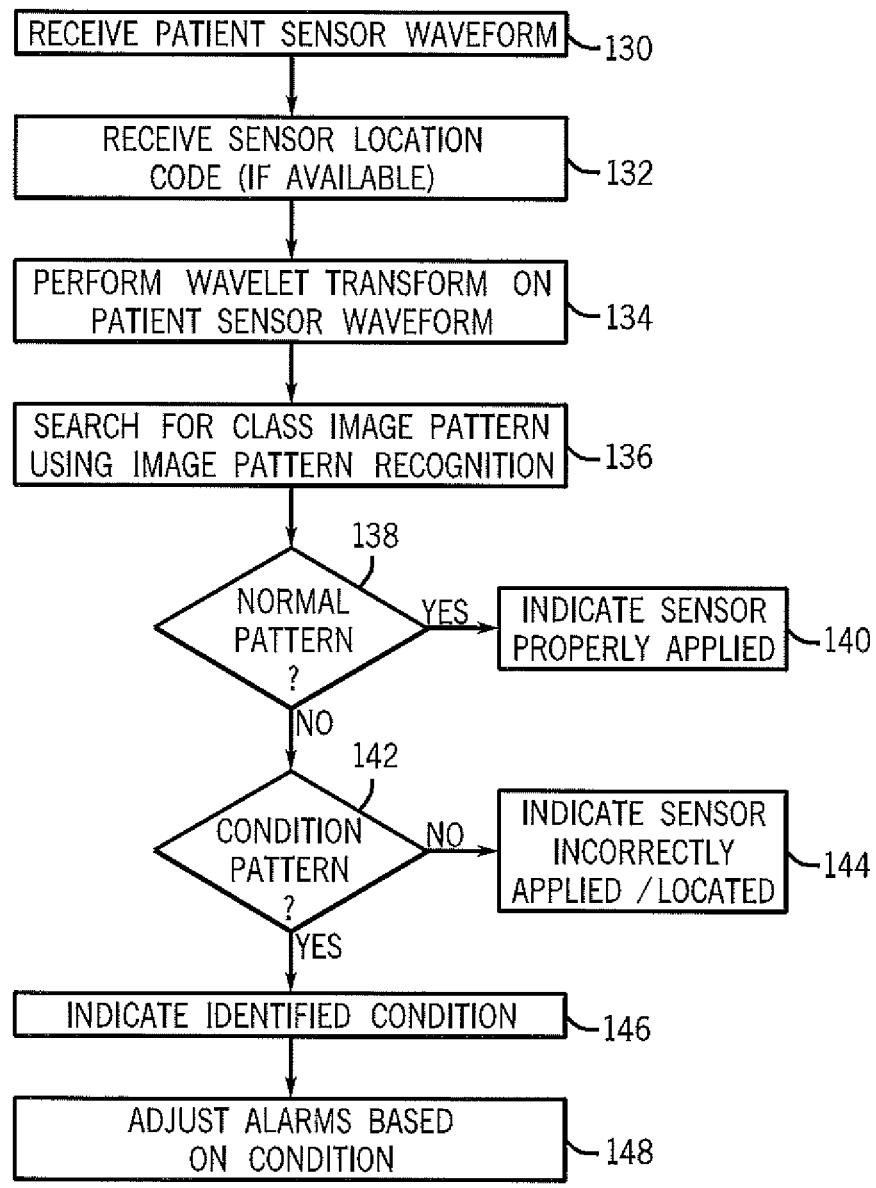
FIG. 16 is a flowchart representing an embodiment of a method for ascertaining sensor application status based on wavelet image pattern detection using the medical sensor system of FIG. 1 after training.

FIGS. 9-16 describe an alternative manner of performing the methods of FIGS. 7 and 8 using the medical sensor system 10. In particular, FIGS. 9-11 describe a manner of using image pattern detection to identify patterns in images, and FIGS. 12-14 describe a manner of transforming physiological information into wavelet images, from which patterns may be identified. FIGS. 15 and 16 represent embodiments of methods for training and using a patient monitor 12 that involve identifying image patterns from wavelet transforms of sensor data.

Figure 9:
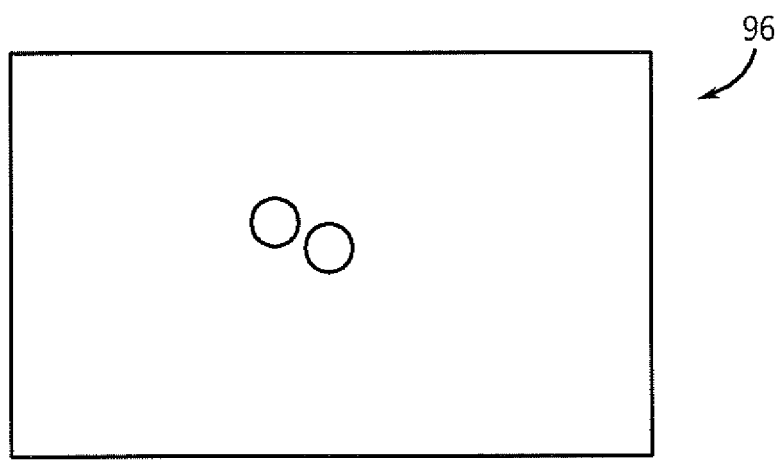
FIGS. 9-11 are schematic illustrations describing a manner of image pattern detection for use by the medical sensor system of FIG. 1, in accordance with an embodiment.

Before turning to FIG. 9, it should be understood that applying certain mathematical transforms to received sensor data may produce multi-dimensional images, or scalograms. Image patterns identifiable in such scalograms may be used both to train a patient monitor 12 and to determine the proper placement of a medical sensor 14, as described below with reference to FIGS. 15 and 16. Using continuous wavelet transformation in one example, the medical sensor 14 may provide sensor data that may be interpreted by the patient monitor 12 as a waveform. The patient monitor 12 may apply one or more wavelet transforms to the waveform to produce an energy map having both time and frequency information. In one embodiment, algorithms or instructions may be implemented or performed by the processor 30 of the patient monitor 12 to transform received sensor signals, such that the signals may be analyzed with respect to time, frequency, and/or magnitude. For example, the wavelet transform of a physiological signal x(t) from the medical sensor 14 may be defined by the relationship below:

$$T(a, b) = \frac{1}{\sqrt{a}} \int_{-\infty}^{+\infty} x(t) \psi * \left(\frac{t-b}{a}\right) dt, \qquad (1)$$

where $\psi^*(t)$ is the complex conjugate of the wavelet function $\psi(t)$, the variable a is the dilation parameter of the wavelet, and b is the location parameter of the wavelet.

In one or more embodiments, any suitable wavelet function, including a Morelet wavelet, may be used to obtain a time-frequency representation of the sensor data. The transform of Equation (1) may be regarded as a time-frequency representation where the characteristic frequency associated with the wavelet is inversely proportional to the scale a, and can be used to construct a representation of a signal on a transform surface. The energy density function of the wavelet transform may be defined by the relationship below:

$$S_R(a, b) = \frac{|T(a, b)|^2}{a}, \qquad (2)$$

where | | is the modulus operator.

By applying a wavelet transform on a time-based signal for the time-frequency representation of the signal, and then applying the energy density function of the wavelet transform, a scalogram may be produced. A scalogram, which also may be interpreted as a spectral density of frequency over time, may be a three-dimensional image (of time, frequency, and magnitude) from which certain physiological patterns may be identified. Certain image patterns in a scalogram may be unique or particularly prevalent among sensor data obtained from medical sensors 14 applied to certain body locations. These patterns may be reliable indicators of location because ongoing or repeated physiological conditions may be characterized by discernible and repeatable patterns, whereas noise, motion artifacts, and other non-repetitive phenomena cannot typically be characterized by a recurring pattern or signature.

Figure 10:
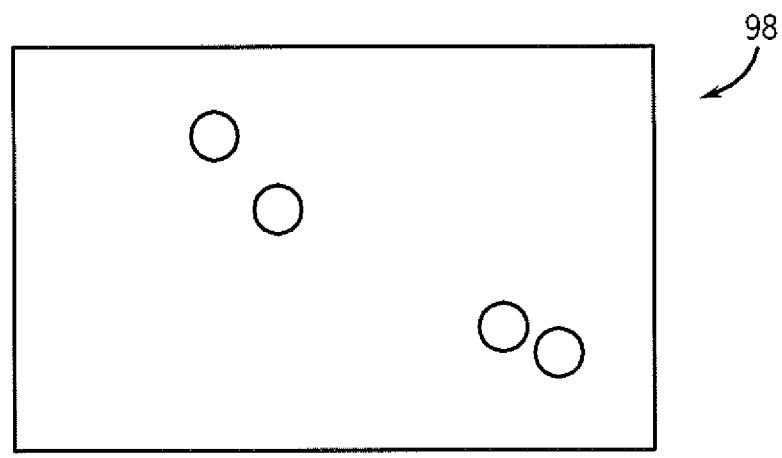
Figure 11:
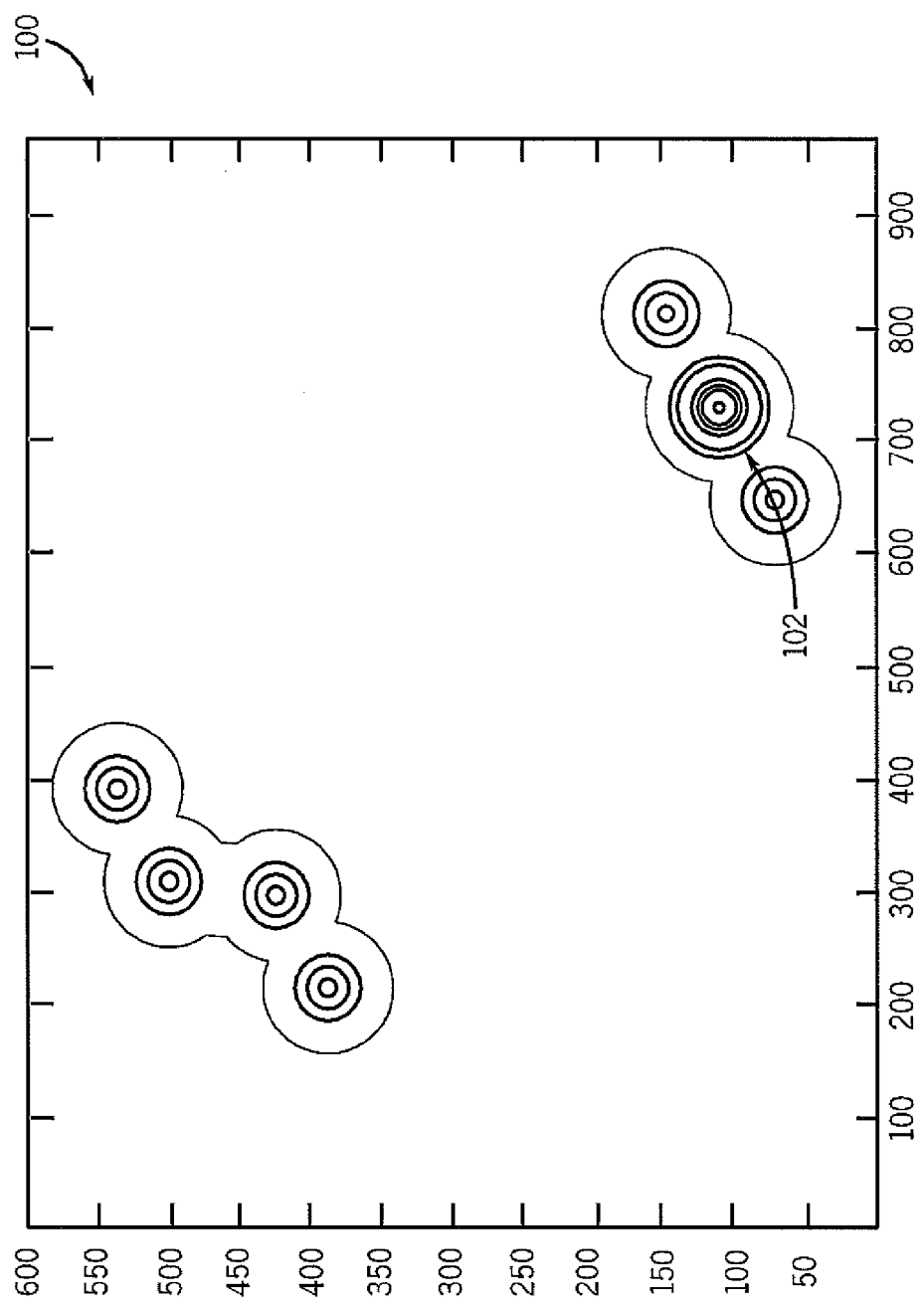

FIGS. 9-11 represent a simplified example of how the patient monitor 12 may analyze images, such as scalograms, to discern such image patterns. The patient monitor 12 may employ such techniques to ascertain classes of sensor data, as well as to determine whether the medical sensor 14 has been properly located and applied, as described in greater detail below. Turning to FIG. 9, a pattern of interest 96 may represent a characteristic associated with sensor data obtained from a particular body location. In FIG. 10, an image 98 may represent a portion of a scalogram deriving from newly-received sensor data from a medical sensor applied to patient 26. The patient monitor 12 may determine whether the pattern of interest 96 is present in the image 98 by cross correlating the pattern 96 with the image 98. FIG. 11 represents an image 100 that may result from such cross correlation. The patient monitor 12 may identify the pattern of interest 96 by setting a threshold to identify the pattern 96 and observing whether the threshold is breached. For example, the threshold may be a spectral intensity, and instances in the image 100 that exceed the threshold intensity may indicate that the pattern 96 is present in the image 98. In the image 100, the presence of a high-intensity locus 102 may identify the pattern 96 in the image 98.

Figure 12:
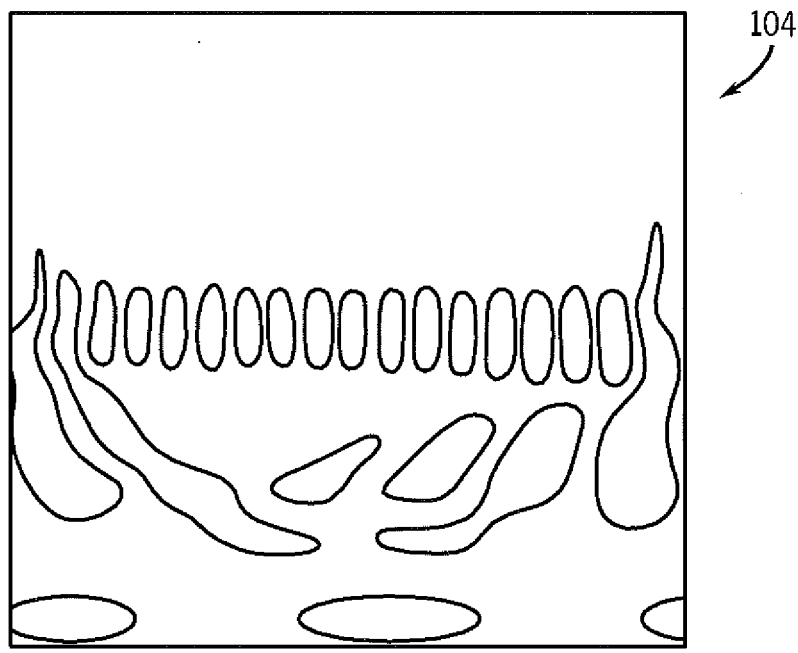
FIGS. 12-14 are schematic illustrations describing a manner of image pattern detection with wavelet transform images from sensor waveforms using the medical sensor system of FIG. 1, in accordance with an embodiment.

FIGS. 12-14 represent another example of how the patient monitor 12 may analyze scalograms to identify patterns of interest. FIG. 12 represents a scalogram 104 that may be obtained by performing a wavelet transform on received sensor data. FIG. 13 represents a wavelet signature 106 that may be present in the scalogram 104. In one embodiment, the scalogram 104 may be cross-correlated with the wavelet signature 106 to determine whether the pattern of interest is present in the scalogram 104. Various techniques, such as the cross correlation and threshold techniques discussed with respect to FIGS. 9-11, may be used to determine whether the pattern, as typified by wavelet signature 106, is present in the scalogram 104. Using such a technique, the patient monitor 12 may process (e.g., cross-correlate) one or more wavelet signatures 106 with the scalogram 104, which may produce an integrated image 108 of FIG. 14. The image 108 may be analyzed (e.g., using image processing techniques and/or facial recognition technologies) to determine whether the patterns are present. In one embodiment, the intensity throughout the image 108 may be analyzed (e.g., using an intensity scale 110) to detect instances where the intensity in the image 108 meets or surpasses a threshold. For example, the present techniques may identify the presence of the wavelet signatures 106 in the scalogram 104 due to the presence of a high-intensity locus 112 that exceeds a threshold intensity.

FIGS. 15 and 16 respectively represent alternative embodiments of the methods described above with reference to FIGS. 7 and 8. In particular, FIG. 15 represents a manner of training the patient monitor 12 using a learning-based algorithm in combination with the image pattern detection techniques illustrated above. FIG. 16 represents a manner in which the patient monitor 12 may identify patterns to ascertain whether a medical sensor 14 has been properly applied to a body location of a patient 26.

As discussed above, sensor data may be collected over a population of patients 26 for which the location and proper application of the sensor 14 is known, and the medical sensor system 10 may use a learning-based algorithm with such collected data to "learn" what sensor data from each location should look like. FIG. 15 is a flowchart 114 describing one embodiment of such a learning-based algorithm. The steps of the flowchart 115 may be implemented in code stored on a tangible machine-readable medium, such as the ROM 38 or non-volatile storage 40.

In a first step 116, the patient monitor 12 may receive sensor data collected from a population of patients 26. Demographic data associated with the collected sensor data may indicate the body location of the sensor 14 from which the data was collected, the age of the patient 26, any conditions or diseases the patient 26 experienced while sensor data was obtained, and so forth. In some embodiments, the collected sensor data may include sensor data obtained simultaneously from two or more medical sensors 14, the combination of which may indicate a relationship that, using the instant technique, may become apparent from the training of the medical sensor system 10. The sensor data received by the patient monitor in step 68 may derive from a database of previously-obtained sensor data, or may be obtained directly from patients 26 monitored by the medical sensor system 10.

In step 118, the patient monitor 12 may perform a mathematical transform, such as the wavelet transform described by Equations (1) and/or (2), on the received sensor data to obtain corresponding images, or scalograms. In step 120, the patient monitor 12 may discern patterns in the images using image processing techniques and/or facial recognition techniques, and in step 122, the patient monitor 12 may cluster the identified patterns into different groups based on similarities in their appearance.

In step 124, the patient monitor 12 may create sensor data classes based on the groups determined in step 122. Step 124 may generally take place in the same manner as step 70 of the flowchart 66 of FIG. 7. After the classes have been ascertained in step 124, the patient monitor 12 may, in step 126, map or associate the identified classes to the body location where sensor data was obtained, any diseases or conditions indicated by the class of sensor data, and/or certain demographic data, in the manner of step 74 of the flowchart 66.

FIG. 16 is a flowchart 128 representing one embodiment of a method for using a patient monitor 12, trained using the technique of FIG. 15, to determine whether a medical sensor 14 has been properly located on and applied to a patient 26 and/or whether the patient 26 has a known condition or disease. In a first step 78, the patient monitor 12 may receive physiological sensor data from a medical sensor 14 applied to a body location of a patient 26. Generally, the physiological sensor data may vary predictably with time, as may occur with a photoplethysmographic waveform. As some medical sensors 14 may transmit a code or other indication to the patient monitor 12 that describes the intended location of the medical sensor, the patient monitor 12 may receive such a code in step 132, which may occur before or after step 130.

In step 134, the patient monitor may perform a mathematical transform, such as the wavelet transform described by Equations (1) and/or (2), on a segment over time of the received physiological sensor data waveform to obtain a current scalogram. In step 136, the patient monitor 12 may compare the current scalogram with the identified classes of patterns stored in the RAM 36, the non-volatile storage 40, and/or an external device. Specifically, in some embodiments, the patient monitor 12 may cross-correlate patterns of interest associated with certain classes and the current scalogram, and a resulting image may be examined for high-intensity loci that exceed a threshold and indicate a match.

From step 132, the patient monitor 12 may have an indication of the intended body location of the medical sensor 14. Thus, as indicated by decision block 138, if the current scalogram shares a pattern of interest associated with a class representing sensor data from medical sensors properly applied to the same body location on healthy individuals, the patient monitor 12 may output an indication that the medical sensor 14 has been properly applied in step 140. The indication may include a message on the display 16, a beep, and/or a flashing light, and so forth.

Turning again to decision block 138, if the current scalogram does not share a pattern of interest associated with the class representing sensor data from medical sensors properly applied to the same body location on healthy individuals, the process may flow to decision block 142. In decision block 142, the patient monitor 12 may next consider whether the current scalogram shares a pattern of interest associated with a class indicating a disease or condition. If not, the patient monitor 12 may conclude that the medical sensor 14 has not been properly applied and, in step 144, may output an indication that the medical sensor 14 has not been properly applied and/or located. If, in decision block 142, the patient monitor 12 does identify a pattern indicative of a disease or condition in the current scalogram, the patient monitor 12 may provide an indication of the identified condition or disease in step 146. The patient monitor 12 may also modify its operation to account for the particular disease or condition in step 148. By way of example, in step 148, the patient monitor 12 may adjust alarm thresholds, increase or decrease sensor data rates, and so forth.

While the embodiments set forth in the present disclosure may be susceptible to various modifications and alternative forms, specific embodiments have been shown by way of example in the drawings and have been described in detail herein. However, it should be understood that the disclosure is not intended to be limited to the particular forms disclosed. The disclosure is to cover all modifications, equivalents, and alternatives falling within the spirit and scope of the disclosure as defined by the following appended claims.

What is claimed is:

1. A patient monitor comprising:
 a medical sensor interface configured to receive physiological data from a medical sensor applied to a patient and to receive from the medical sensor an indication of a proper body location of the patient to which the medical sensor is to be applied; and
 data processing circuitry configured to be trained, using a learning-based algorithm, to determine whether the received physiological data indicates that the medical sensor has been properly applied to the patient.

2. The patient monitor of claim 1, wherein the data processing circuitry is configured to be trained, using the learning-based algorithm, to determine whether the received physiological data indicates that the medical sensor has been applied to the proper body location of the patient.

3. The patient monitor of claim 1, wherein the data processing circuitry is configured to be trained, using the learning-based algorithm, to determine whether the received physiological data indicates that the patient has a disease or a condition.

4. The patient monitor of claim 1, wherein the data processing circuitry is configured to be trained, using the learning-based algorithm, by receiving physiological data obtained from a plurality of medical sensors applied to known body locations of a plurality of patients and determining classes of physiological data associated with the known body locations.

5. The patient monitor of claim 1, wherein the data processing circuitry is configured to determine whether the medical sensor has been properly applied to the patient by comparing the received physiological data to one or more classes of physiological data associated with known body locations.

6. The patient monitor of claim 1, wherein the physiological data from the medical sensor comprises photoplethysmographic data, temperature, respiration rate, blood pressure, electrocardiogram data, or pulse transit time sensors, or any combination thereof.

7. A method comprising:
 receiving, onto data processing circuitry, medical sensor data obtained from one or more medical sensors properly applied to one or more known body locations;
 determining, using the data processing circuitry, one or more classes of sensor data characteristics associated with proper application of the one or more medical sensors to the one or more known body locations;

storing, onto a memory device, the one or more classes of sensor data characteristics, wherein the medical sensor data is derived from a plurality of patients with one or more known medical conditions and wherein at least one of the one or more classes of sensor data characteristics is associated with the one or more known medical conditions;

receiving subsequent medical sensor data obtained from a medical sensor applied to a patient onto the data processing circuitry and comparing the subsequent medical sensor data to the one or more classes to determine whether the patient has one of the one or more known medical conditions; and changing alarm limits associated with the received medical sensor data when the patient is determined to have one of the one or more known medical conditions.

8. The method of claim 7, wherein the one or more classes of sensor data characteristics represent particular values, time-dependent changes detected in the medical sensor data, or frequency-dependent changes detected in the medical sensor data, or any combination thereof.

9. The method of claim 7, comprising receiving the subsequent medical sensor data obtained from the medical sensor applied to the patient onto the data processing circuitry and comparing the subsequent medical sensor data to the one or more classes to determine whether the medical sensor has been properly applied to the patient.

* * * * *